United States Patent [19]

Witkin

[11] Patent Number: 4,935,248

[45] Date of Patent: Jun. 19, 1990

[54] ANTIMICROBIAL VETERINARY COMPOSITIONS AND METHODS

[75] Inventor: Roy T. Witkin, Westport, Conn.

[73] Assignee: Albert L. Jacobs, New York, N.Y.; a part interest

[21] Appl. No.: 225,262

[22] Filed: Jul. 28, 1988

[51] Int. Cl.$^5$ .................. A61K 7/20; A61K 31/79; A61K 33/18; A61K 33/40

[52] U.S. Cl. .................. 424/616; 424/51; 424/53; 424/670; 424/671

[58] Field of Search .................. 424/51, 53, 150, 616, 424/670, 671

[56] References Cited

U.S. PATENT DOCUMENTS

| | | | |
|---|---|---|---|
| 3,639,574 | 2/1972 | Schmolka | 424/616 |
| 3,728,449 | 4/1973 | Cantor et al. | 424/670 |
| 3,903,265 | 9/1975 | Meisch | 424/616 |
| 3,954,974 | 5/1976 | Herzog et al. | 424/616 |
| 4,088,597 | 5/1978 | Morlock et al. | 424/671 |
| 4,113,857 | 9/1978 | Shetty | 424/150 |
| 4,130,640 | 12/1978 | Chazan et al. | 424/671 |
| 4,151,275 | 4/1979 | Cantor et al. | 424/671 |
| 4,401,651 | 8/1983 | Knutson | 424/150 |
| 4,402,937 | 9/1983 | Denzinger et al. | 424/150 |
| 4,521,403 | 6/1985 | Simon et al. | 424/53 |
| 4,526,751 | 7/1985 | Gartner | 424/678 |
| 4,557,935 | 12/1985 | Ekenstam et al. | 424/616 |
| 4,567,036 | 1/1986 | Simon et al. | 424/53 |
| 4,592,487 | 6/1986 | Simon et al. | 424/53 |
| 4,592,489 | 6/1986 | Simon et al. | 424/53 |
| 4,597,975 | 7/1986 | Woodward et al. | 424/150 |
| 4,654,208 | 3/1987 | Stockel et al. | 514/252 |
| 4,738,840 | 4/1988 | Simon et al. | 424/150 |
| 4,746,451 | 5/1988 | Hachmann et al. | 424/616 |

FOREIGN PATENT DOCUMENTS 659698  10/1951  United Kingdom ............... 424/616

*Primary Examiner*—Shep K. Rose
*Attorney, Agent, or Firm*—Jacobs & Jacobs

[57] ABSTRACT

In the technology of applying, spraying, or sponging antimicrobially effective amounts of aqueous iodophor peroxide solutions to the udder surfaces of cows, or other animals to be milked prior to milking, the present invention comprises the improvement which avoids iodides and staining which consists essentially of the step of shampooing said udders with a non-staining shampoo containing (a) from about 0.5% to 2% of iodine in a povidone-iodine complex and (b) about 0.5% to 5% of hydrogen peroxide as a nascent oxygen source, said individual components (a) and (b) being combined, with water, at the time of use and having been maintained dry and out of contact with one another in a container or receptacle.

1 Claim, No Drawings

ANTIMICROBIAL VETERINARY COMPOSITIONS AND METHODS

The present invention relates to an antimicrobial veterinary composition and method comprising an iodophor and a peroxide in aqueous solution and the treatment of large and small animals therewith. The peroxide provides nascent oxygen which enhances the antimicrobial activity of the iodine derived from the iodophor. The preferred iodophor is the povidone iodine complex and the preferred peroxide in $H_2O_2$. While the amounts and relative proportions may be varied depending on the animal and the treatment, the amount of derived iodine is about 0.5% to 1% to 2%, of weight, and the percentage of nascent oxygen is about 0.5% to 5% calculated on the weight of $H_2O_2$ as the nascent oxygen source, the balance being substantially all water. The large animals are cows, pigs, etc and the small animals are cats or dogs, etc.

BACKGROUND OF THE INVENTION

Combinations of iodophors and peroxides for the treatment of periodontal and oral disorders are known and have been found to be effective particularly for the combatting of plaque and for cidal action against microbes in the human oral cavity and for preventive or curative purposes during or after surgery as exemplified by U.S. Pat. No. 4,567,036 and related patents of which I am a co-inventor.

THE PRESENT INVENTION

I have now discovered that aqueous or aqueous alcoholic solutions of iodophors and peroxides are useful for veterinary purposes in the treatment of large and small animals against a wide spectrum of microbes afflicting such animals or to which such animals are exposed. Due to their ready availability and reasonable costs I prefer to use povidone-iodine complex and $H_2O_2$ in aqueous solution for application to the large and small animals such as cows, pigs, cats and dogs. The amounts and relative proportions of the components may be varied but preferably the aqueous antimicrobial solution when freshly prepared contains about 0.5% to 1% to 2% of iodine derived from the povidone-iodine complex and about 0.5% to 5% of nascent oxygen calculated on the weight of $H_2O_2$ as the nascent oxygen source.

The invention is illustrated by the following non-limitative examples:

EXAMPLE 1

Cows to be milked by an automatic or mechanical milking machine are treated by spraying or sponging their udders and then milked. The minimum amount of antimicrobial composition is applied to avoid any contamination of the milk and only enough to treat the udder surfaces. While the composition is substantially non-staining should any udder coloration be observed the treatment can be considered effective as it requires only a very short contact since the composition acts virtually instantaneously. Any slight udder coloration also assures that sterilization has occurred. The composition can also be used for conventional hand milking, if desired, in which even the person doing the milking should wear gloves the surfaces of which have been pre-treated with the composition to sterilize those portions of the gloves which come in contact with the udders of the cow or other lactating animal whose milk is to be removed.

Bovine Mastitis is the condition that can be best addressed. This disorder occurs in two forms: clinical or sub-clinical, both of which are contagious and spread from cow to cow during milking. The resultant effect is to spread bacteria in milk in high enough numbers as &:o make the product unsafe for consumption. Causative microorganisms are: Streptococcus, Staphylococcus and Coliforms. Specific organisms implicated in contagious mastitis are: Staph. Aureus, Strep. Agalactiae, Mycoplasma. Other microbes present may include: Fungi (Yeasts and Molds) and algae.

EXAMPLE 2

Skin diseases of animals can be effectively treated with the composition by clipping the hair around the infected area(s) and applying the composition as a shampoo. Two skin diseases susceptible to such treatment are *streptrothricosis* or *dermatophilosis* in cattle and *trichophvto verrucosum* ringworm.

EXAMPLE 3

Animals that live or stand in stalls containing manure or unclean soil commonly become afflicted with lameness and/or nail bed infection known as foot rot caused by infectious organisms in moist manure—littered soil, characteristically caused by injury or puncture. Application of the antimicrobial composition overcomes these conditions. Best results are obtained by a subsequent daily or twice daily foot bath in the composition which type of treatment is also recommended as a preventative.

EXAMPLE 4

In many large animals the anal orifice is above the vagina so that resultant vaginal infections occur and represent a serious problem for veterinary gynecologic medicine. These infections can be overcome by the use of a vaginal douche of the present composition.

EXAMPLE 5

The present antimicrobial composition is useful and effective in sheep or animal dips by forcing the animal to walk through a bath of the composition. The treatment can take the form also of a tick and/or insect control method.

EXAMPLE 6

The present antimicrobial composition can also be used in the treatment of cat and dog (household pets) disorders or infections and since it is undesirable to change the color of the household pets the original or residual color is maintained by adjusting the proportions of the composition by weighting the solution on the oxygen side wherein the povidone iodine/peroxide ratio is 1:2 or 1:3.

Ear infections are common problems with household pets usually picked up by the spread of bacteria from dirt to paws to ear (otic infections) via scratching a flea or tick bite. Otic use is carried out by administering the PVP-I/peroxide ratio above set forth to the site of the flea or tick bite which is apparent from the actions of the household pet.

EXAMPLE 7

The present antimicrobial composition is moreover useful for first-aid and generalized antiseptic treatment of household pets in aqueous solution, ointment or salve form. Indications for use for household pets is essentially the same as for human antisepsis in the treatment of a broad spectrum of microbial disorders including bites and scratches from other animals, control of infection from insect bites and generally traumatic injuries and wounds.

EXAMPLE 8

The antimicrobial compositions of the present invention may be formulated as a dentifrice both to aid in the removal and prevention of plaque but to combat odor-causing bacteria. Any suitable dentifrice base may be use with which the antimicrobial composition is admixed or combined. The dentifrice may contain glucose oxidase and lactoperoxidase which can replace the peroxide e.g. $H_2O_2$ in my formulation.

The foregoing description and examples are intended as illustrative and not limitative since various changes and modifications may be made without departing from the scope of the invention. While the source of nascent oxygen has been set forth as $H_2O_2$ are calculated on the basis of the nascent oxygen derived from the $H_2O_2$, it is understood that other peroxides may be used as the source of nascent oxygen such as benzoyl peroxide and other compounds having an extra oxygen atom which under the conditions of the treatments of the large and small animals provide nascent oxygen which acts to increase or enhance the antimicrobial activity of the iodine of the iodophor. The preferred iodophor is the povidone iodine complex but other known iodophors may be substituted.

It is further understood that prior to the preparation of the veterinary composition as an aqueous solution comprising an iodophor and a peroxide the individual components are maintained out of contact with one another until the aqueous solution is to be prepared and used. This may be accomplished in any suitable manner such as by means of a compartmented container or other partitioned receptacle in which each compartment contains one of the components. It is undesirable and results in a loss of potency if the components are prematurely combined. The povidone iodine complex is a brownish powder which is very soluble in water whereas elemental iodine is insoluble or only very slightly soluble in water since the polymeric povidone acts as a solubilizer for the iodine. By following this procedure the iodine derived from the povidone iodine complex avoids the formation of iodides which while themselves readily soluble in water are unsuitable for the purposes of the present invention.

What is claimed is:

1. In the technology of applying, spraying, or sponging antimicrobially effective amounts of aqueous iodophor or peroxide solutions to the udder surfaces of cows, or other animals to be milked prior to milking, the improvement which avoids iodides and staining which consists essentially of the step of shampooing said udders with a non-staining shampoo containing (a) from about 0.5% to 2% of iodine in a povidoneiodine complex and (b) about 0.5% to 5% of hydrogen peroxide as a nascent oxygen source, said individual components (a) and (b) being combined, with water, at the time of use and having been maintained dry and out of contact with one another in a container or receptacle.

* * * * *